(12) United States Patent
Kasai et al.

(10) Patent No.: US 6,881,316 B2
(45) Date of Patent: Apr. 19, 2005

(54) CAPILLARY ARRAY DEVICE

(75) Inventors: Syouzou Kasai, Hitachinaka (JP);
Yoshiyuki Okishima, Higashiibaraki (JP); Tomonari Morioka, Hitachinaka (JP); Yasushi Shimizu, Hitachinaka (JP); Hiroyuki Tanaka, Hitachinaka (JP); Takayasu Furukawa, Hitachinaka (JP); Noriyuki Shimoda, Higashimurayama (JP); Seiichi Ugai, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 344 days.

(21) Appl. No.: 10/190,481

(22) Filed: Jul. 9, 2002

(65) Prior Publication Data

US 2002/0179446 A1 Dec. 5, 2002

Related U.S. Application Data

(62) Division of application No. 10/100,009, filed on Mar. 19, 2002.

(30) Foreign Application Priority Data

Apr. 2, 2001 (JP) .......................................... 2001-103274

(51) Int. Cl.$^7$ ............................................... G01N 27/453
(52) U.S. Cl. ........................................ 204/604; 204/601
(58) Field of Search ................................. 204/601, 604, 204/451, 453

(56) References Cited

FOREIGN PATENT DOCUMENTS

| JP | 10-206382 | 8/1998 | |
|---|---|---|---|
| JP | 2000-227413 | 8/2000 | |
| WO | WO 99/00664 A1 * | 7/1999 | .......... G01N/27/26 |

* cited by examiner

Primary Examiner—Alex Noguerola
(74) Attorney, Agent, or Firm—Dickstein Shapiro Morin & Oshinsky LLP

(57) ABSTRACT

The present invention easies a connection between electrodes of a capillary array device and a connection plate for supplying a high voltage to the electrodes.

According to the present invention, a connection plate 23 and hollow electrodes 20 are connected without solder but via a spring force. Alternatively, the hollow electrodes 20 can be connected to the connection plate 23 by utilizing volume elasticity of the connection plate.

32 Claims, 20 Drawing Sheets

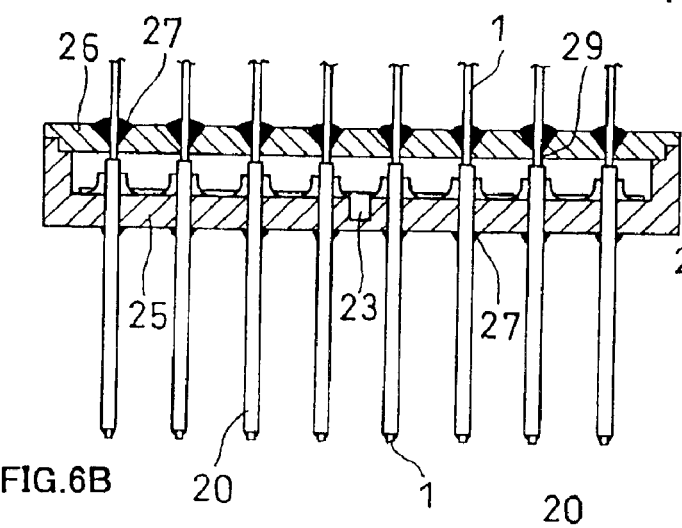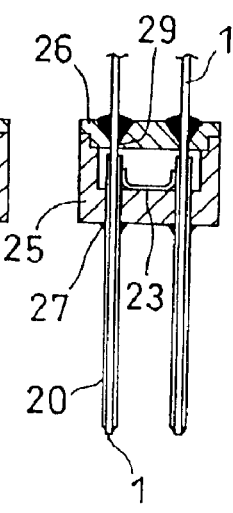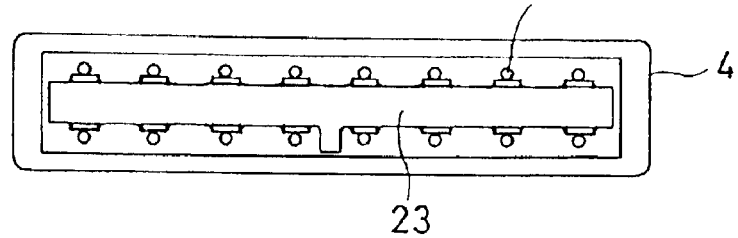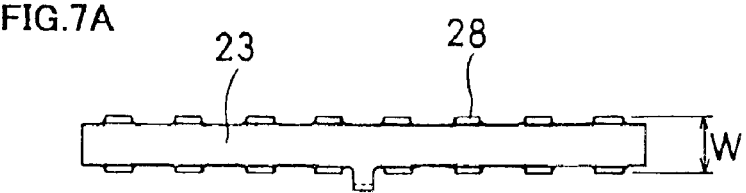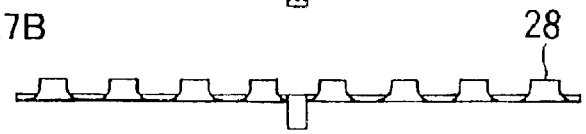

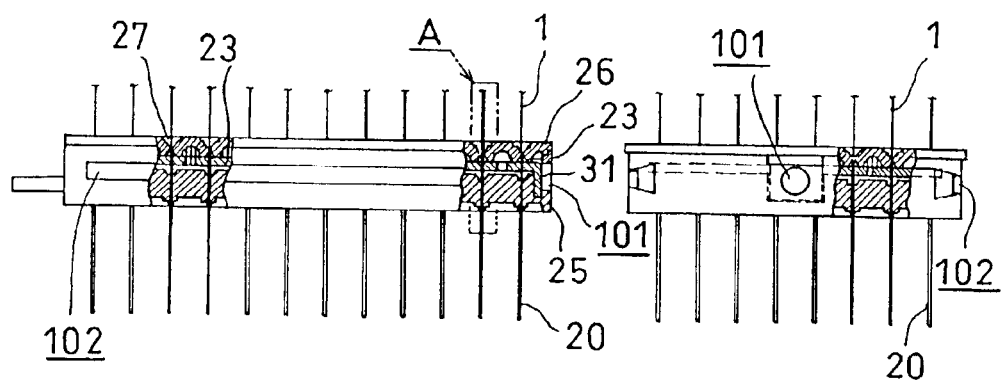
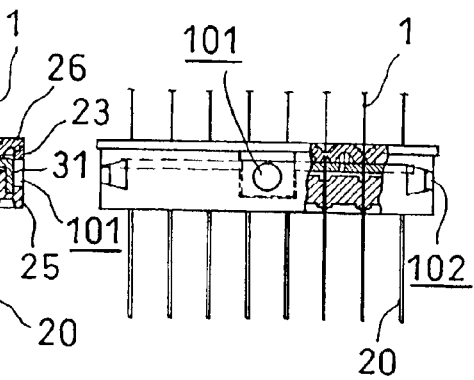
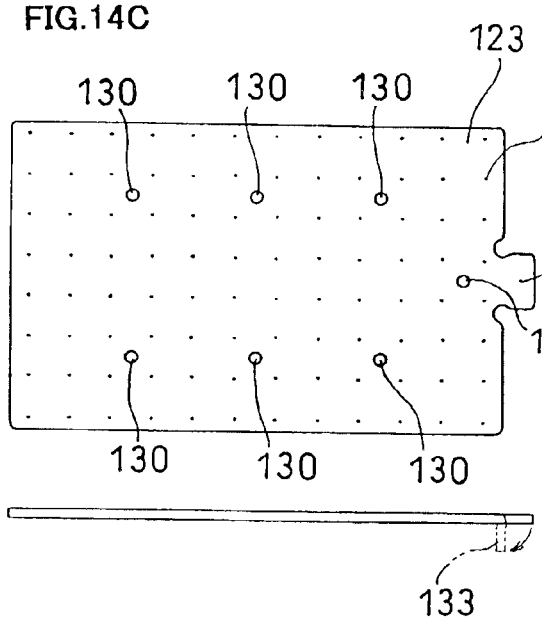
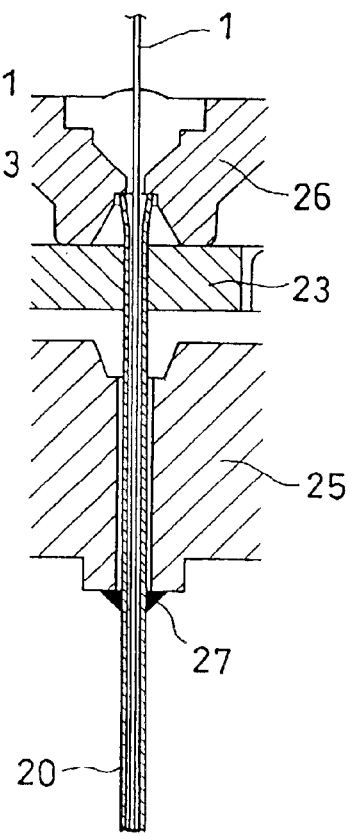

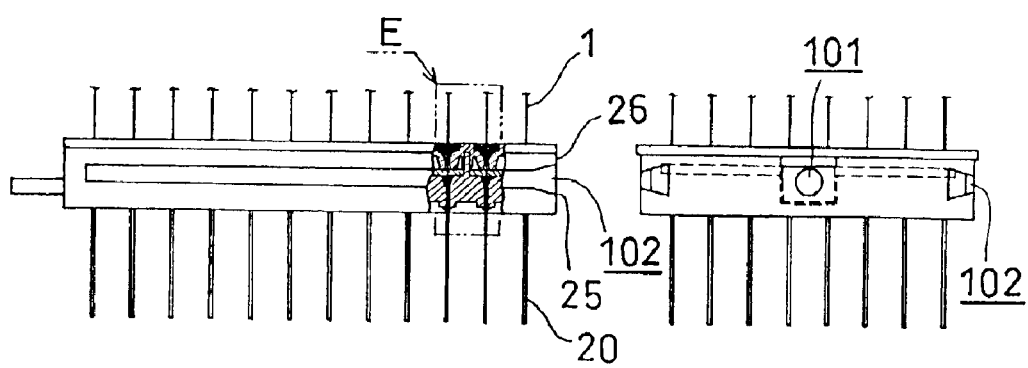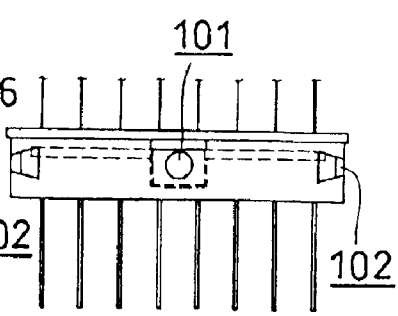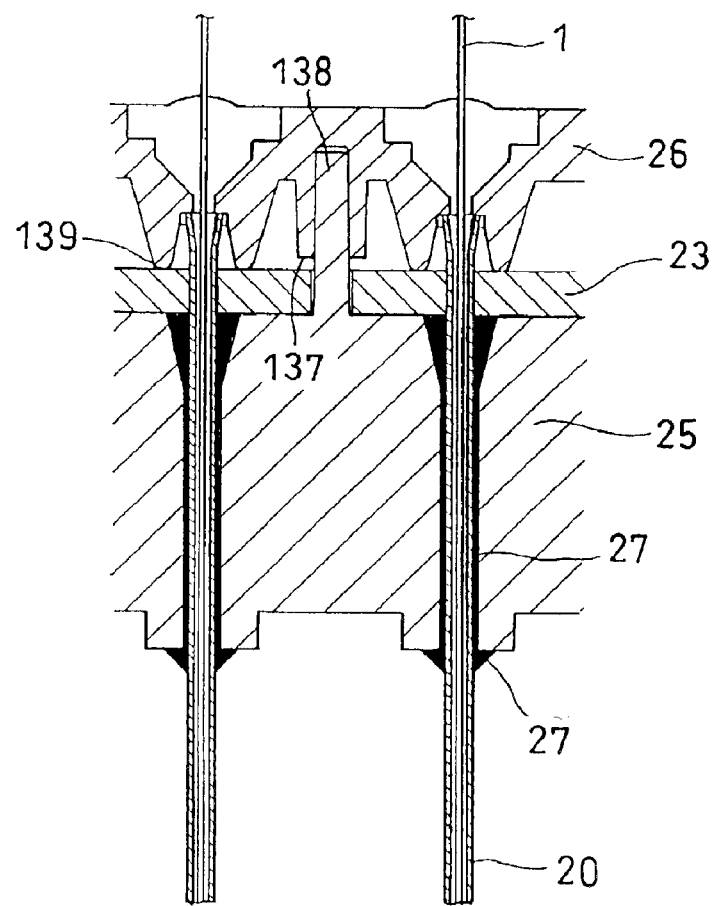

CAPILLARY ARRAY DEVICE

This application is a divisional application of U.S. patent application Ser. No. 10/100,009, filed Mar. 19, 2002.

FIELD OF THE INVENTION

The present invention relates to a capillary array electrophoresis apparatus for separating and analyzing a sample such as DNA and a protein, to a capillary array incorporated in the electrophoresis apparatus, and to a method for producing the capillary array.

BACKGROUND OF THE INVENTION

A technique is well known in which a capillary device incorporating a combination of a plurality of capillaries is used for supplying and running an electrophoresis medium together with a sample to be analyzed or separated to utilize a target sample for separation and analysis. In addition, a technique where a sample such as fluorescence-labeled DNA or protein is supplied to a capillary is described, for example, in U.S. Pat. Nos. 5,366,608, 5,529,679, 5,516,409, 5,730,850, 5,790,727, 5,582,705, 5,439,578 and 5,274,240. In view of the throughput for separation and analysis, use of multi-capillaries is more advantageous than an electrophoresis method employing a flat gel. Japanese Patent Laid-Open Application No. 9-96623 describes a capillary array electrophoresis apparatus.

FIG. 2 is a perspective view for illustrating a capillary array device. Each of capillaries 1 has an outer diameter of 0.1 to 0.7 mm and an inner diameter of 0.02 to 0.5 mm, and is coated with a polyimide resin. The capillary array device is formed with an arrangement of a plurality (generally, several to several-tens) of capillaries which are quartz pipes. The capillary array device is further provided with a load header 4 for drawing fluorescence-labeled DNA samples or the like from sample reservoirs into the respective capillaries by electrophoresis, a separator 16 for aligning the plurality of capillaries, a detector (window unit) 5 for firmly holding the capillaries 1 in the order of the sample numbers at the load header 4, and a capillary head 17 for bundling and holding the plurality of capillaries together. The load header 4 is provided with hollow electrodes 20 for applying an electrophoresis voltage to the capillaries. The detector (window unit) 5 is provided with an aperture for irradiating the arrangement of capillaries and an aperture from which the light from the capillaries comes out. According to the present invention, the detector 5 can be any detector as long as parts of the plurality of capillaries to be irradiated with laser light (parts of the capillaries where they allow transmission of the laser light for exciting the sample) can be held in parallel.

FIG. 3 is a schematic view showing an electrophoresis system. The sample inlet ends of the capillaries 1 and the hollow electrodes 20, which are protruding from the load header 4 of the capillary array device shown in FIG. 2 are immersed into a sample tray 3 which includes a plurality of sample reservoirs 2 each containing a fluorescence-labeled DNA sample. The other ends of the capillaries 1 at the capillary head 17 are attached to a buffer reservoir 14 containing a buffer 13 by pressure-proof sealing. A high voltage of about 15 kV from a high-voltage power source 15 is applied to the buffer reservoir 14 and the load header 4, whereby the samples in the sample reservoirs are subjected to electrophoresis for sample separation with the buffer 13 from the buffer reservoir 14 supplied into the capillaries 1.

A laser light source 6 radiates excitation light to the detector (window unit) 5 via an excitation optical system including mirrors 7, a beam splitter 8, convergence lenses 9 and the like. The excitation light irradiation allows fluorescence 10 as signal light output from the samples running through the capillaries 1 to be detected by a CCD camera 12 via a detection lens system 11. The detected signal is processed by a signal processing unit 21.

In the exemplary electrophoresis system shown in the figure, laser light is radiated to both sides of the capillary array device containing DNA or proteins to be electrophoresed. The laser light is converged by means of lens function of the capillaries so that all of the capillaries are irradiated with the excitation light, whereby fluorescence from each capillary is detected by the detection optical system.

The load header 4 samples the samples and also serves as the hollow electrodes 20 on the sample reservoir side for applying a high voltage between the samples and the buffer reservoir 14. FIGS. 4A and 4B are schematic views showing a structure of a conventional load header. Sixteen capillaries 1 are each inserted into the respective hollow electrodes 20 made of narrow stainless steel (hereinafter, simply referred to as "SUS") pipes, and fixed with an epoxy adhesive 27. The sample side ends of the capillaries 1 are slightly protruding from the hollow electrodes 20. As shown in FIGS. 5A and 5B, the sixteen hollow electrodes 20 are arranged on a holding frame 22, aligned with a connection plate 23 with a strict margin, and are bonded to the connection plate 23 with solder 24. SUS pipe electrodes are used because the samples or reagents to be separated and analyzed are corrosive.

The bonded hollow electrodes 20 and the connection plate 23 are incorporated into a plastic holder 25. A lid 26 is fixed onto the holder 25 by ultrasonic bonding. Then, the holder 25 and the hollow electrodes 20 are sealed and fixed from outside with an adhesive 27, thereby achieving a complete load header. The capillaries 1 are sealed in the lid 26 by the adhesive 27 so as to prevent them from slipping out and to avoid high voltage leak. The connection plate 23 is partially bent by 90° so as to allow connection to a high-voltage contact (not shown) via the aperture in the holder 25.

The capillary array device is an expendable item that looses desirable characteristics after being used for several-tens of times.

The above-described conventional load header has the following problems.

(1) Load header assembly requires a number of operations such as adhesion and bonding, which requires time and results in production at a high cost.

(2) Operations such as adhesion and bonding requires skill of the operator, and are sensitive to operation conditions and environment, which results in poor reliability.

(3) Since a strong acid soldering flux is used for soldering the connection plate and the SUS electrodes, the flux becomes ionic impurities, thereby deteriorating electrophoresis. Therefore, the narrow electrodes need to be washed both inside and outside by high-quality washing.

SUMMARY OF THE INVENTION

The present invention has an objective of cleanlily producing an inexpensive load header for a capillary array device, which introduces samples into the capillary array device and which applies a high voltage for electrophoresis. Furthermore, the present invention has an objective of producing a load header having a long-lasting reliable structure.

In one aspect of the present invention, the above-described objectives are achieved by electrically connecting a plurality of electrodes and a connection plate incorporated in a load header of a capillary array device via a spring connection instead of soldering. In order to decrease the number of operations for adhesion, a plastic holder and the electrodes are integrally molded by integration molding, thereby improving reliability. Furthermore, in order to improve reliability of the contact parts, the contact parts are covered with an adhesive or a conductive adhesive to be shielded from atmosphere, thereby preventing an oxide film having large electrical resistance from being generated on the surface of the contact parts.

Specifically, a capillary array device of the present invention comprises: a plurality of capillaries; a window unit for holding the arrangement of the plurality of capillaries in the middle of the length of the capillaries, the window unit provided with an aperture for radiating light to the arrangement of capillaries and an aperture from which the light from the capillaries comes out; a load header for holding the plurality of capillaries and a plurality of electrodes at a sample inlet end; and a capillary head for holding the plurality of capillaries at the other end, wherein the load header is provided with a holder, the plurality of hollow electrodes fixed to the holder, and a conductive connection plate that makes contact with the outer surfaces of the plurality of hollow electrodes via spring force; and the plurality of capillaries are passed through the respective hollow electrodes such that the tips of the capillaries are exposed from the hollow electrodes.

Preferably, the hollow electrodes and the connection plate are made of austenite stainless steel such as SUS304 or SUS316, which is highly resistant to corrosion.

Preferably, the edges of the connection plate and the outer surfaces of the hollow electrodes are electrically connected so as to enhance a pressure at the contact interfaces.

Preferably, a plurality of nail springs of the connection plate, which are symmetrically provided around each of the hollow electrodes, make contact with the outer surfaces of the hollow electrodes.

Preferably, the inscribed circle formed by each set of nail springs of the connection plate is smaller (preferably, by about 70 to 85%) than the outer diameter of each of the hollow electrodes, and the connection plate is inserted from the upper ends of the hollow electrodes for assembly.

Preferably, a pressure at the contact interfaces between the outer surfaces of the hollow electrodes and the nail springs of the connection plate is 5 to 10 MPa.

The connection plate may be made of metal, a conductive rubber plate or conductive plastic.

Preferably, the hollow electrodes are made integrally with the holder by integration molding.

Furthermore, the spring contact parts between the connection plate and the hollow electrodes may be shielded from atmosphere.

Specifically, the spring contact parts may be applied with an adhesive to be shielded from atmosphere. The adhesive may be a conductive adhesive. Preferably, the conductive material of the conductive adhesive is nickel particles, and the adhesive is an epoxy adhesive.

Another aspect of the invention is a capillary array electrophoresis apparatus and a capillary array in which a plurality of hollow electrodes which, together with sample inlet ends of capillaries, are immersed in samples make close contact with and are electrically connected with a conductive connection plate by the volume elasticity of the connection plate. Preferably, the hollow electrodes are secured in holes formed in the elastic connection plate. By doing so, the hollow electrodes can be secured in the connection plate by being inserted therethrough. Since the connection plate and the hollow electrodes press each other, contact resistance can be minimized.

Yet another aspect of the invention is a method for producing a load header by arranging an elastic connection plate between a holder having a plurality of hollow electrodes and a lid, and pressing the holder and the lid toward each other. By doing so, the hollow electrodes and the connection plate are electronically connected, and the holder and the lid are bonded, thereby producing a load header. Preferably, the load header is designed such that the parts of the connection plate near the hollow electrodes are pressed by the holder and the lid after the completion of the load header. As a result, pressure bonding between each hollow electrode and the connection plate can be enhanced.

BRIEF DESCRIPTION OF THE DRAWINGS

FIGS. 6A to 6C are schematic views showing an example of a structure of a load header that gains an electric connection between the electrodes and the connection plate via fastening force of a spring;

FIGS. 7A to 7C are schematic views showing the shape of the connection plate;

FIGS. 14A to 14D are views showing a load header according to Embodiment 2;

FIGS. 20A to 20C are views showing the load header according to Embodiment 3.

DETAILED DESCRIPTION OF THE INVENTION

Figure 1A:
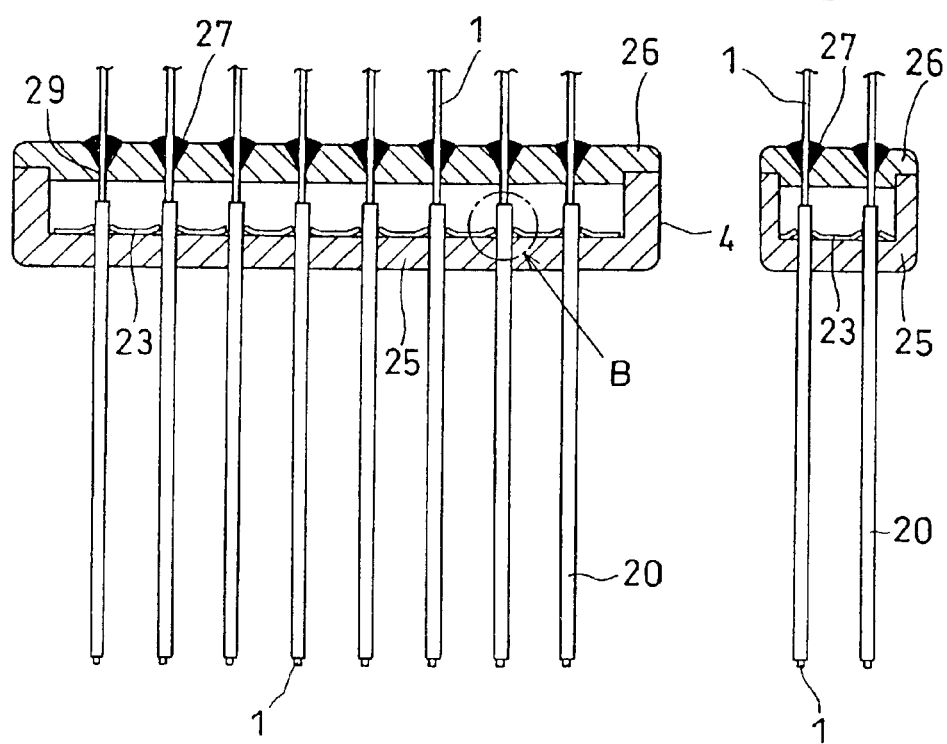
FIGS. 1A to 1D are schematic views showing an example of a load header according to the present invention.

Hereinafter, embodiments of the present invention will be described with reference to the drawings.

Embodiment 1

FIGS. 6A to 6C are schematic views showing one example of a load header structure where hollow electrodes and a connection plate are electrically connected by a fastening force of springs. FIG. 6A is a front cross-sectional view of the load header; FIG. 6B is a plan view of the load header without the lid; and FIG. 6C is a side cross-sectional view of the load header.

FIGS. 7A to 7C are schematic views showing a shape of the connection plate incorporated into the load header shown in FIGS. 6A to 6C. FIG. 7A is a plan view; FIG. 7B is a front view; and FIG. 7C is a side view of the connection plate, respectively.

As can be appreciated from FIGS. 6A to 6C, sixteen hollow electrodes 20 in two rows are accurately fixed to the holder 25 with an adhesive 27, and the connection plate 23 shown in FIGS. 7A to 7C is pushed in between the two rows of hollow electrodes 20. The width w of the connection plate 23 is about 10% wider than the width between the two rows of hollow electrodes 20 so that a spring force is generated between the U-shaped contact parts 28 and the hollow electrodes 20, thereby obtaining a desirable pressure at the interfaces therebetween. After pushing the connection plate 23 in between the two rows of hollow electrodes 20 fixed to the holder 25, a lid 26 is placed and bonded. The capillaries 1 are inserted into the respective hollow electrodes 20 via capillary guiding holes 29 in the lid 26, thereby assembling the load header. Thus, a load header structure can be obtained without using a solder.

This structure, however, was found to have the following problems.

(1) The hollow electrodes 20 may be bent toward outside due to the spring force of the connection plate 23, which causes a shift between the capillary guiding holes 29 in the lid 26 and the hollow electrodes 20 upon bonding the lid 26. As a result, the capillaries 1 may not allow the hollow electrodes 20 to pass therethrough.

(2) The pressure the interfaces may fluctuate due to the variation of the inside measurement between the two rows of hollow electrodes 20. As a result, contact resistance in a humidity test or a vibration test may greatly fluctuate.

Figure 1B:
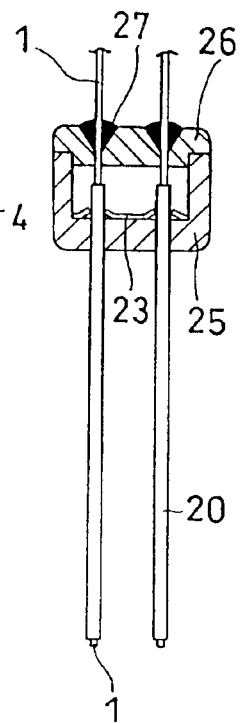
Figure 1C:
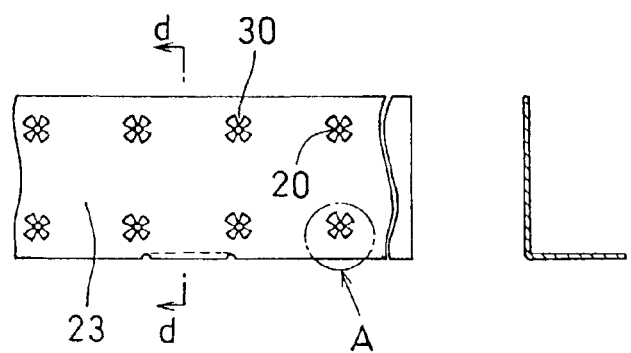
Figure 1D:
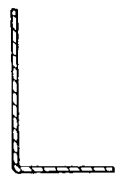
Figure 2:
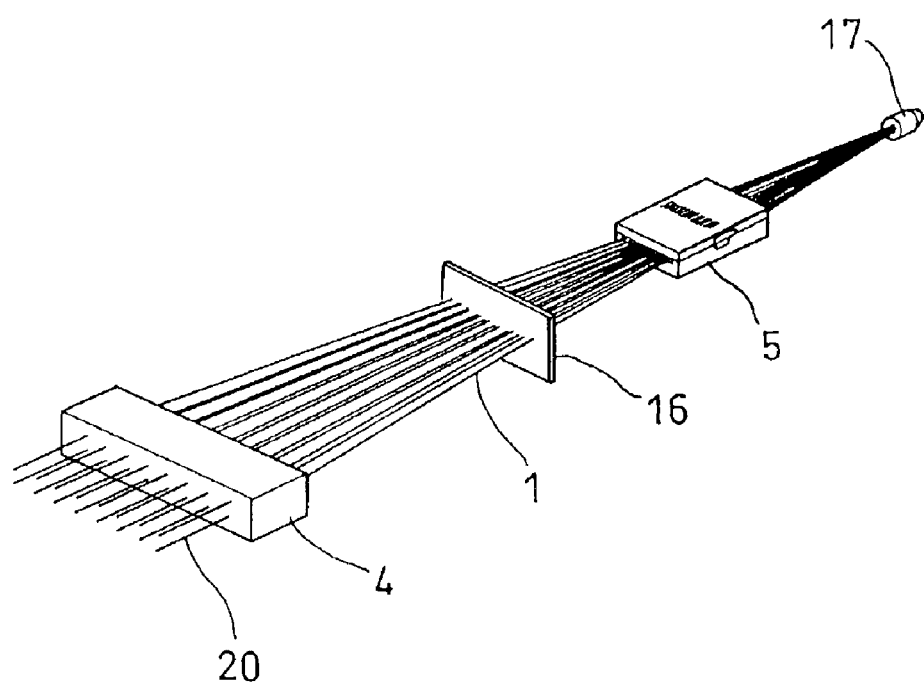
FIG. 2 is a perspective view for illustrating a capillary array device.
Figure 3:
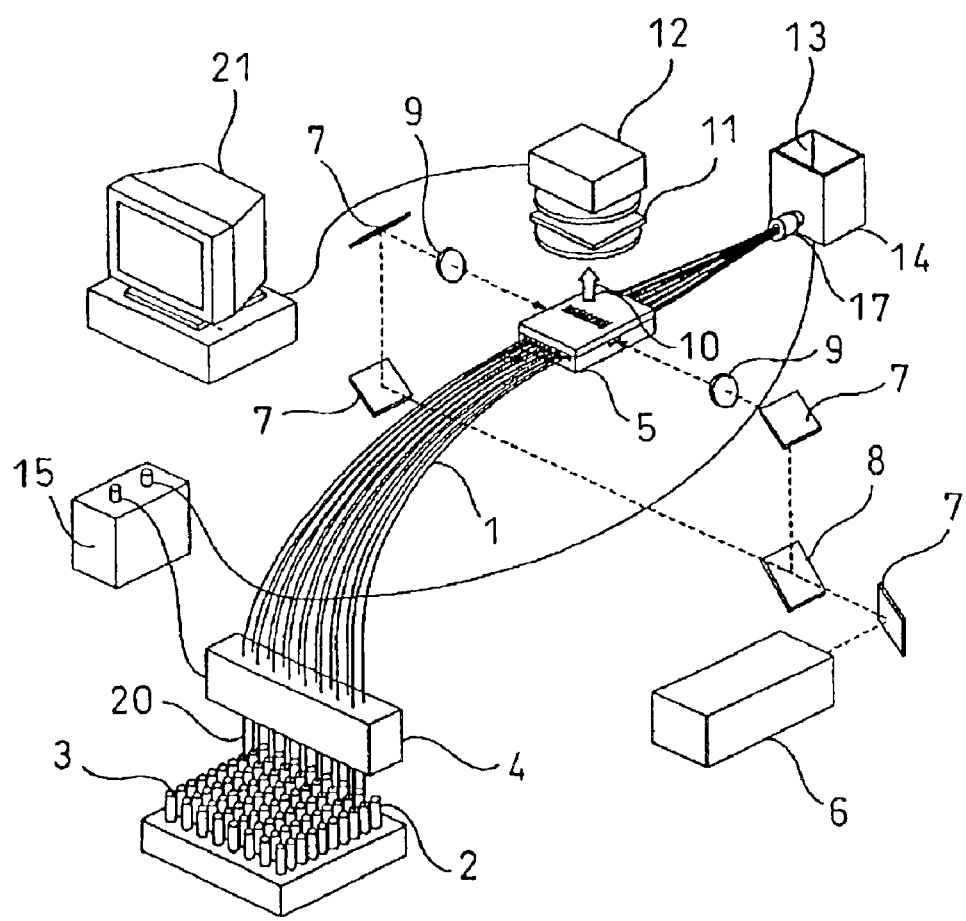
FIG. 3 is a schematic view showing an electrophoresis system.
Figure 4A:
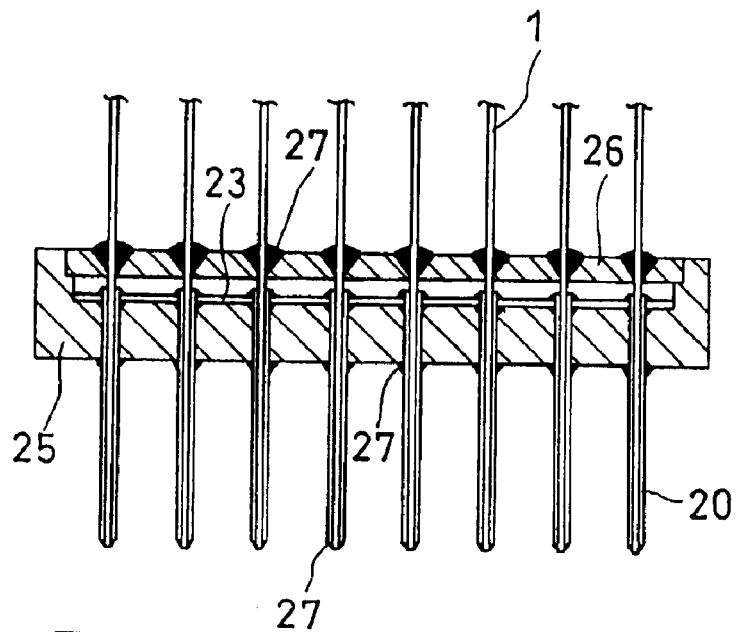
FIGS. 4A and 4B are schematic views showing a structure of a conventional load header.
Figure 4B:
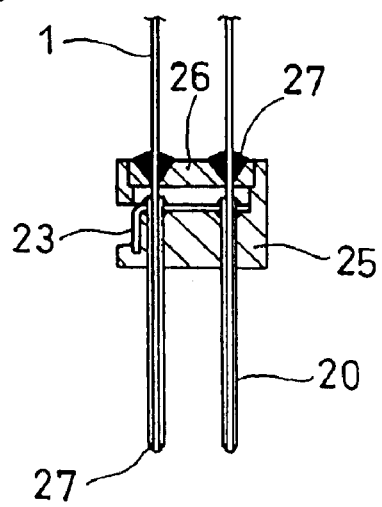
Figure 5A:
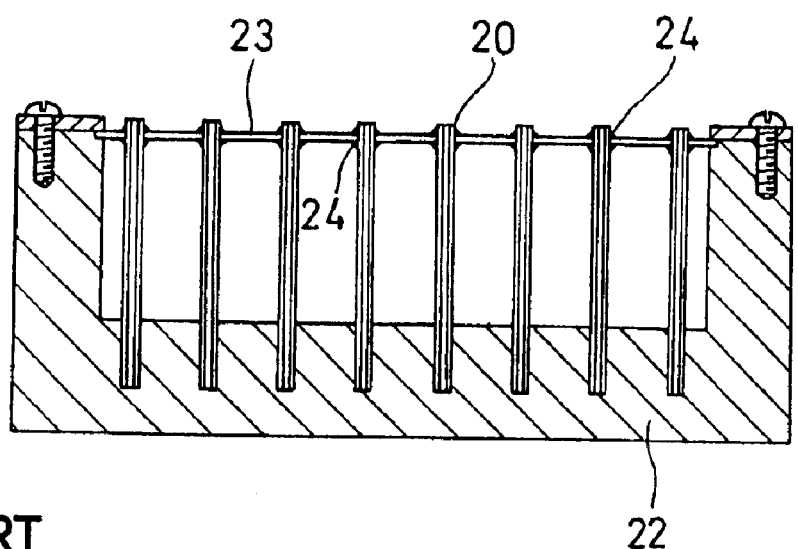
FIGS. 5A and 5B are schematic views for illustrating a conventional device.
Figure 5B:
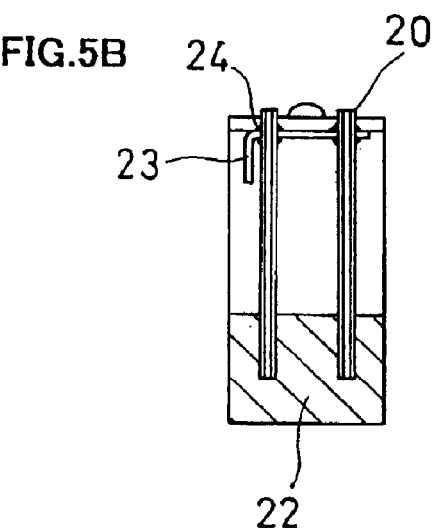

FIGS. 1A to 1D are schematic views showing an example of a preferable load header that has solved the above-mentioned problems. FIG. 1A is a cross-sectional view of the load header; FIG. 1B is a side cross-sectional view of the load header; FIG. 1C is a plan view showing an essential part of the connection plate; and FIG. 1D is a cross-sectional view cut along line d—d in FIG. 1C.

The holder 25 is made together with austenite electrodes as the hollow electrodes 20 by injection molding so that the hollow electrodes 20 are integrated with the holder 25. Accordingly, the step of bonding the hollow electrodes 20 to the holder 25 can be skipped. For injection molding, an upper part and a lower part of a die for forming the holder are provided with holes for receiving the hollow electrodes. Thus, a resin is forced into the die while the hollow electrodes are set into the die for integration. If the surfaces of the electrodes are contaminated, the hollow electrodes can easily slip out. Therefore, it is important to use sufficiently washed electrodes. The injection pressure of the resin is 40–60 MPa, and the temperature of the die differs depending on the type of the resin used. The resulting hollow electrodes 20 and the holder 25 have good dimension precision. According to conventional methods, the distortion of the electrodes needed to be mended after the bonding, whereas integration molding does not require such mending, which is greatly effective in reducing the cost.

The connection plate 23 has a plurality of nails 30 as contact parts arranged in a symmetric manner around the respective electrode as shown in FIG. 1C so that no force that bends the hollow electrodes 20 is caused. The connection plate 23 is an SUS plate made of the same austenite as the hollow electrodes 20 in order to enhance the spring force and protection against corrosion.

Hereinafter, a method for attaching the connection plate will be described. The connection plate 23 is placed on the holder 25 that has been integrated with the hollow electrodes 20 so as to match the inner diameters of the sixteen hollow electrodes 20 with the respective centers of the contact parts.

Figure 8:
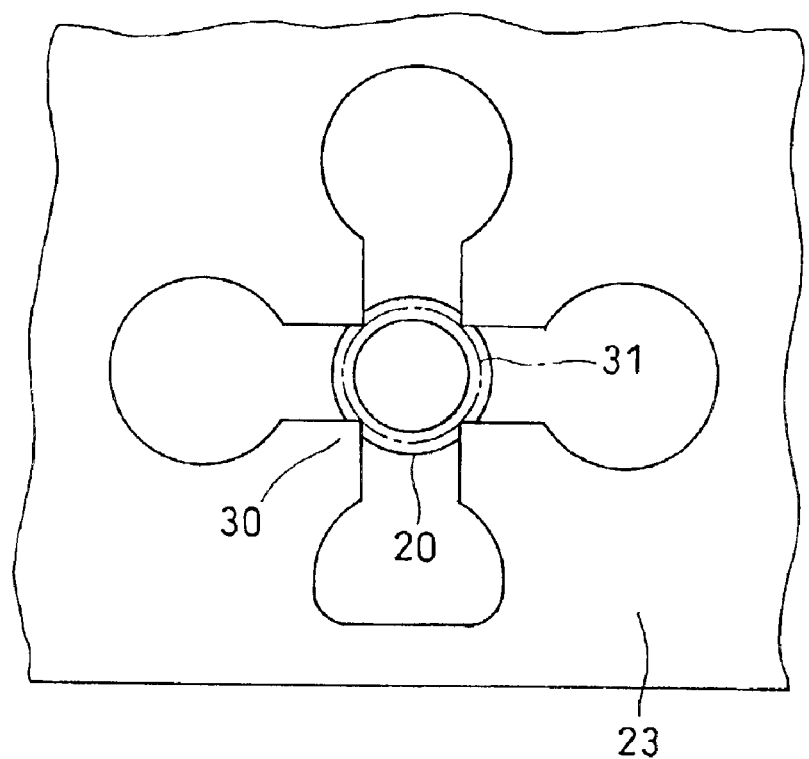
FIG. 8 is an enlarged view of the top of the contact parts.

FIG. 8 is an enlarged view of part A in FIG. 1C, showing an enlarged plan view of one of the contact parts. The dashed circle in the figure indicates an inscribed circle 31 of the four nails 30. The inscribed circle 31 is smaller than the outer diameter of the hollow electrode 20 by about 20% so that a spring characteristic can be obtained after assembly.

Figure 9:
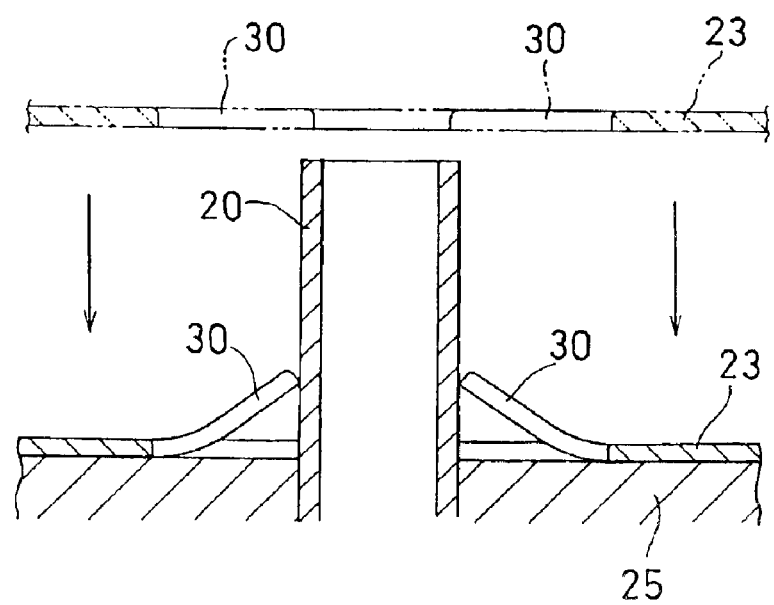
FIG. 9 is a side view of the contact parts of an electrode and the connection plate.

FIG. 9 is an enlarged view of part B in FIG. 1A, showing an enlarged side view of one of the hollow electrodes 20 and the connection plate 23.

The connection plate 23 is pushed in the direction indicated by the arrows while the outer surface of the hollow electrode 20 and the nails 30 scratch each other. At this point, the passive state coatings on the surfaces of both the hollow electrode and the nails are torn off, thereby establishing a metal connection between them. The connection plate 23 is formed through press work by being punched out in the direction indicated by the arrows shown in FIG. 9 so that, as can be appreciated from the cross-sectional view of the nails 30, the nails 30 have edges at the bottom surface, by which the pressure at the interfaces becomes larger. Suitable number of the nails 30 is three to six, although it depends on the size and the technique for processing the contact parts. The pressure at the interfaces at this point is 5–10 MPa, and an exceeding value will deform the hollow electrodes 20, interfering the capillaries 1 from entering into the hollow electrodes 20. The contact resistance is 0.05 Ω to several Ω, confirming little fluctuation during an environment test such as a corrosion gas test or a humidity test. Although the tips of the nails 30 are squared shape in FIG. 8, in practice, no difference is made in the contact resistance when the tips of the nails 30 have a roundness of about 0.2 R.

The pressure P at the interfaces between the outer surfaces of the hollow electrodes 20 and the nails 30 of the connection plate 23 can be calculated by the following equation:

$$P=F/S$$

where F is the force of the nails 30 pressing the hollow electrode 20, and S is the contact area.

Figure 10:
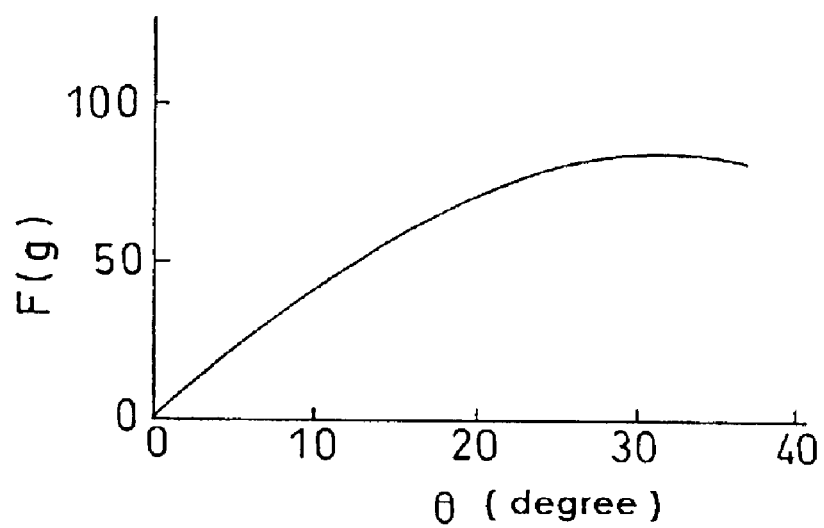
FIG. 10 is a graph showing a relationship between the bent angle of a nail and the force of the nail pressing the electrode.

Here, the contact area S is about 0.5 to $1.0 \times 10^{-4}$ cm$^2$, and force F is 45 to 65 grams. F is obtained by a stress analysis of the relationship between the bending angle and the force of the nails 30, whose results are shown in FIG. 10. Herein, the nails 30 are made from a stainless plate having a thickness of 0.2 mm, and the length of the nails 30 and the diameter of the hollow electrode 20 are chosen to obtain a bent θ of 12–15 degrees. The pressure P at the contact interface thus becomes 4.4 MPa to 12.7 MPa, and therefore a contact pressure P within an inner range of 5–10 MPa is preferable.

Examples of alternative material for the connection plate 23 include non-metal materials such as conductive rubber and conductive plastic. In this case, the shape of the contact parts may be round or polygonal. The contact parts are practically designed such that they allow contact resistance of several Ω to several-hundreds of Ω.

Figure 11A:
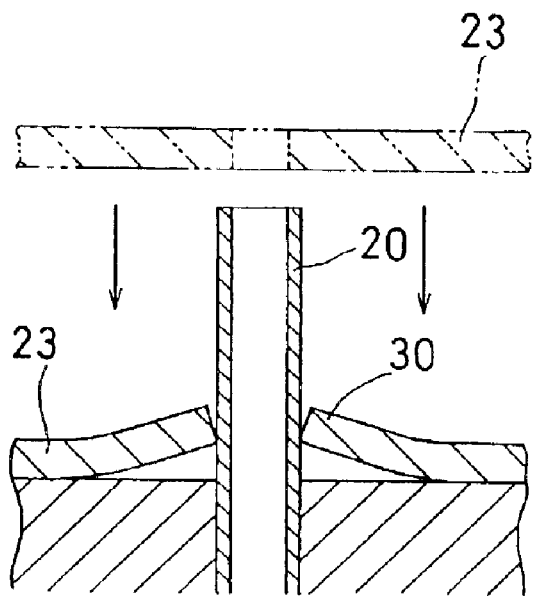
FIGS. 11A and 11B are schematic views showing an example of a connection plate made of conductive rubber.
Figure 11B:
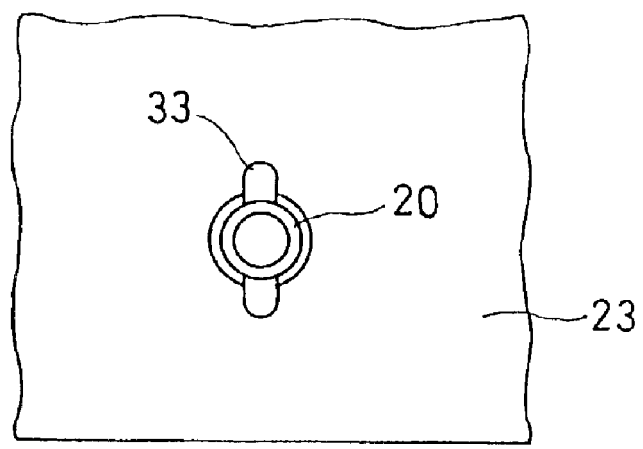

FIGS. 11A and 11B are cross-sectional view and a plan view, respectively, of an exemplary connection plate 23 made of conductive rubber. A rubber material having a thickness of 0.5 to 1.0 mm is added with carbon powder and metal powder to gain conductivity. The nail has an inscribed circle opening that is about ¼ to ¾ of the outer diameter of the hollow electrode 20. The opening is pushed down from the top of the hollow electrode 20 in the direction indicated by the arrows in the figure. Even when the upper part of the hollow electrode has a flared shape whose diameter is larger than the diameter of the rest of the part of the hollow electrode by 20–30%, rubber is highly flexible and thus the same effect as the spring can be obtained. Split cuts 33 in the nail are provided for aiding the insertion of the connection plate. Preferably, the rubber material is NR, NBR or EPDM rubber. The hardness can be set to 70 or higher in order to increase the spring characteristic of the rubber, thereby obtaining a high contact pressure.

Figure 12A:
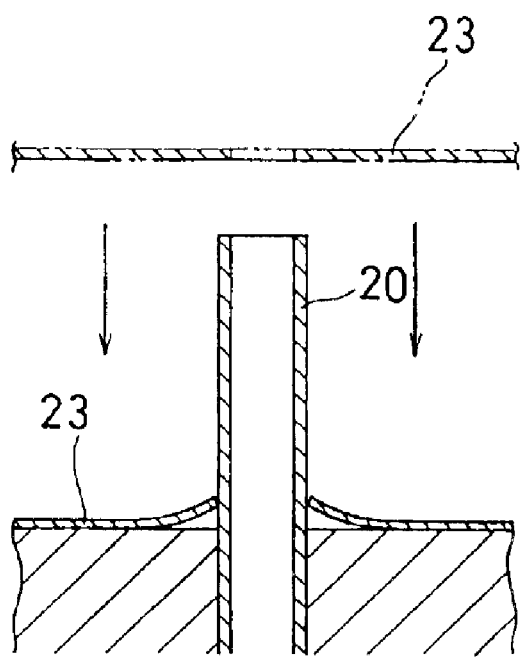
FIGS. 12A and 12B are schematic views showing an example of a connection plate made of conductive plastic.
Figure 12B:
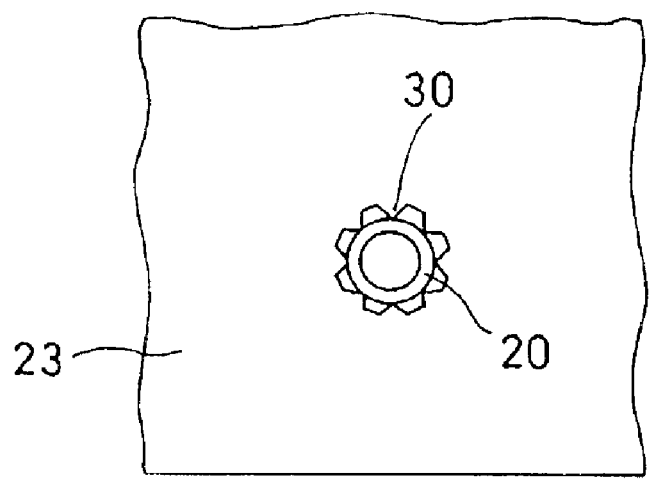

FIGS. 12A and 12B are a cross-sectional view and a plan view, respectively, showing an example of a connection plate 23 made of conductive plastic. The conductive plastic generally has a thickness of about 0.1 mm, and may be, for example, polyacetylene, metal-powder-mixed plastic, a metal-plated film or a metal-deposited film. FIGS. 12A and 12B show a case where a plurality of contact nails 30 are provided inside the circle opening. Instead of the circle opening, cuts may be made to obtain an electric connection.

Thus, by making the connection plate 23 from a non-metal material such as conductive rubber and conductive plastic, stable characteristics can be obtained with little plastic deformation even though the nails are greatly deformed. In addition, there is an advantage in that the connection plate can be produced with an inexpensive die.

When the capillary array device is used under more severe environment or transportation conditions, or when an appropriate pressure at the contact interfaces cannot be obtained due to structural requirements, the contact parts are preferably shielded from oxidizing atmosphere or moisture so as to prevent a passive state film to be formed on the interface between the SUS contact parts of the hollow electrodes 20 and the nails 30 of the connection plate 23. Thus, stable contact resistance can be maintained.

Figure 13A:
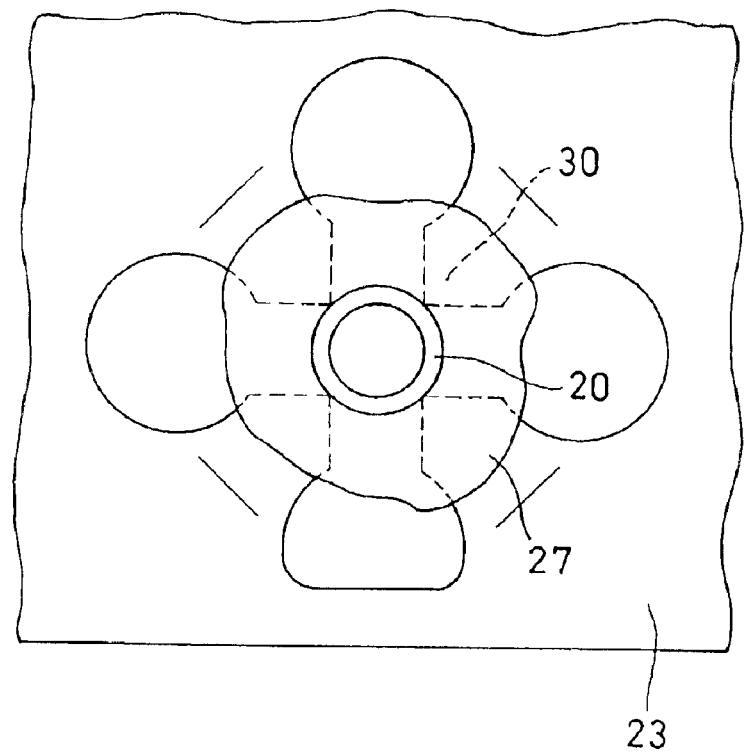
FIGS. 13A and 13B are schematic views showing an example for shielding the contact parts of the connection plate and the electrode from atmosphere.
Figure 13B:
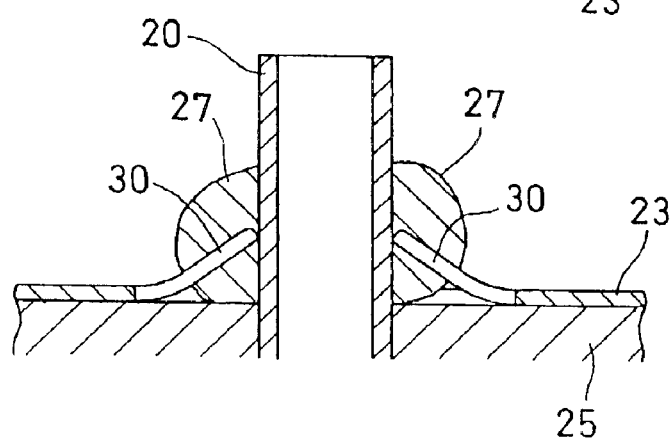

Specifically, as shown in FIGS. 13A and 13B, an adhesive 27 is applied and cured on the interface between the SUS contact parts of the hollow electrodes 20 and the nails 30 of the connection plate 23, thereby shielding the contact parts from oxidizing atmosphere and moisture. Accordingly, generation or increase of a passive state film can be prevented, thereby maintaining stable contact resistance. This effect is doubled since the contact parts are secured with the adhesive 27. An adhesive is generally made of an insulator material. For safeness consideration, the adhesive may be a conductive adhesive 27 containing conductive particles. Preferably, the conductive particles are nickel particles. Most appropriately, the adhesive is an epoxy adhesive which is inexpensive, and has a strength and well water-proof characteristic.

Embodiment 2

The present embodiment relates to a load header in which hollow electrodes are inserted through a connection plate and held there by volume elasticity of the connection plate, and a method for producing the load header. The present embodiment will be described with reference to FIGS. 14 to 18.

FIGS. 14A to 14D are views showing the load header according to the present embodiment. FIG. 14A is a partial front cross-sectional view of the load header; FIG. 14B is a partial side cross-sectional view of the load header; FIG. 14C is a schematic view of the connection plate and FIG. 14D is a detailed view of part A in FIG. 14A.

The load header is provided with: ninety-six hollow electrodes 20; a connection plate 23 bonded with the ninety-six hollow electrodes and connected to a high-voltage contact of an electrophoresis apparatus to apply a high voltage to the hollow electrodes; a plastic holder 25 for accommodating the connection plate with the hollow electrodes 20 arranged in a matrix of 8×12; a lid 26 fixed on the holder 25 by ultrasonic bonding; a high-voltage terminal plug 101 for applying a high voltage to the hollow electrodes 20; and a concave guide 102 for engaging and connecting the load header to the electrophoresis apparatus.

For attaching the load header to the electrophoresis apparatus, a convex rail of the electrophoresis apparatus is fitted in the concave guide 102. The high-voltage contact of the electrophoresis apparatus is plugged into the high-voltage terminal plug 101 to be able to apply a high voltage to the hollow electrodes 20 for electrophoresis. The high-voltage terminal plug 101 is a hole formed in the holder 25 through which a tag 133 of the connection plate 23 is exposed outside the load header.

Ninety-six capillaries 1 are inserted into the hollow electrodes 20 which are narrow stainless steel pipes, with the sample side ends of the capillaries 1 being slightly exposed from the hollow electrodes. The capillaries 1 are fixed in the hollow electrodes 20 with an epoxy adhesive 27. SUS pipes are used as the hollow electrodes because samples and reagents used for separation and analysis are corrosive.

The connection plate 23 is a plate member with insertion holes (insertion positions) 131 arranged in a matrix of 8×12 for the hollow electrodes 20 to pass therethrough as shown in FIG. 14C. The connection plate 23 is also provided with holes 130 which engage with guide pins 128 of the holder 25 to prevent positional shift between the holder 25 and the connection plate 23. The connection plate 23 also has the tag 133 for connecting with the high-voltage contact. The connection plate is made of a material having elasticity and conductivity, and preferably is made of conductive rubber.

As shown in FIG. 14D, each hollow electrode 20 is passed through the corresponding insertion hole (insertion position) 131 of the elastic connection plate 23 and is secured there with the hollow electrode pressing out the elastic insertion hole 131. More specifically, the outer surfaces of the hollow electrodes 20 and the inner surfaces of the respective insertion holes (insertion positions) 131 of the connection plate 23 make close contact with each other with enhanced degree of bonding due to the elasticity (volume elasticity) of the connection plate 23. Thus, the contact resistance between the hollow electrodes and the connection plate becomes small and thus uniform. As a result, separation ability of each capillary is ensured to be constant. In addition, there is no need of welding each hollow electrode to the connection plate.

The hollow electrodes are secured to the holder by inserting the hollow electrodes into the holes of the holder whose diameters are larger than that of the hollow electrodes, and by filling the gap with an adhesive 27. The adhesive is deposited on the top surface of the holder to reach the bottom surface of the holder so as to ensure the gaps to be sealed. In general, removing liquid in a narrow gap is difficult due to the capillary effect and thus a sample existing in the gap may cause contamination. In the present example, however, there is no gap between the holder and the hollow electrodes and thus such contamination can be avoided.

Figure 15A:
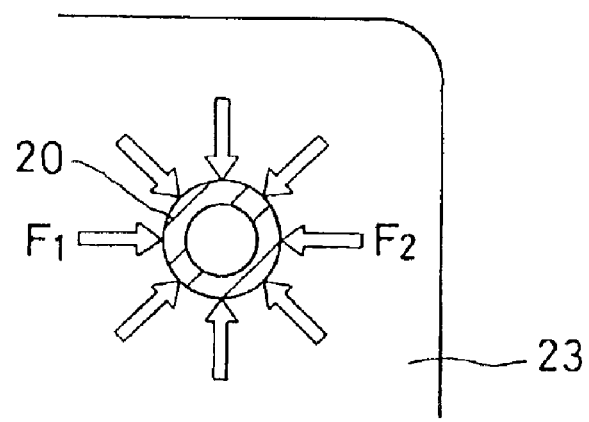
FIGS. 15A and 15B are schematic views showing the force put by the connection plate to the hollow electrodes.
Figure 15B:
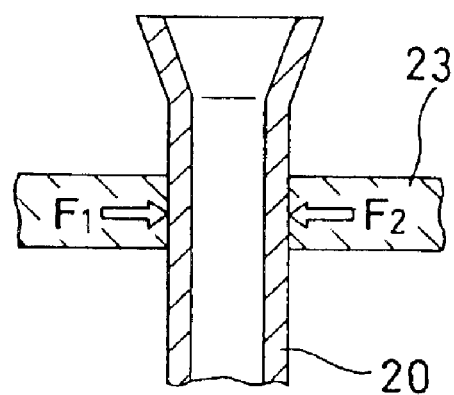

FIGS. 15A and 15B are schematic views showing how the force caused by the volume elasticity of the connection plate is applied to the hollow electrodes. As shown in FIG. 15A, the hollow electrode is held by being squeezed by the volume elasticity at a plurality of opposing points (F1, F2) of the connection plate. In particular, when the entire circumference of the outer surface of the hollow electrode is making contact with the connection plate, the hollow electrode will receive elasticity from every direction which restores the position of the hollow electrode even when a load is applied to the hollow electrode in a certain direction. Especially when the cross-section of the hollow electrode is circular, the hollow electrode will receive equal restoring force (elasticity) equally from every direction, which enhances restoring ability.

The tag 133 as a part of the connection plate is bent such that the face of the tag that is to make contact with the high-voltage contact is perpendicular to the direction for attaching the load header to the electrophoresis apparatus, thereby simplifying the mechanism for attaching the high-voltage contact. The high-voltage contact is directly connected to the tag 133. Unlike the case where the contact is indirectly connected with the tag 133 via a conductive member such as a metal member, this can avoid a problem of variations in the contact resistance of the intervening conductive member. Since the hollow electrodes of the present embodiment are electrically connected to the high-voltage contact via the connection plate only, the problem of variations in the contact resistance of the intervening conductive member can be avoided. As a result, not only the separation abilities among the capillaries but the separation abilities among the capillary arrays can be made uniform.

Hereinafter, a method for producing the load header of the present embodiment will be described with reference to FIGS. 16 to 18.

Figure 16A:
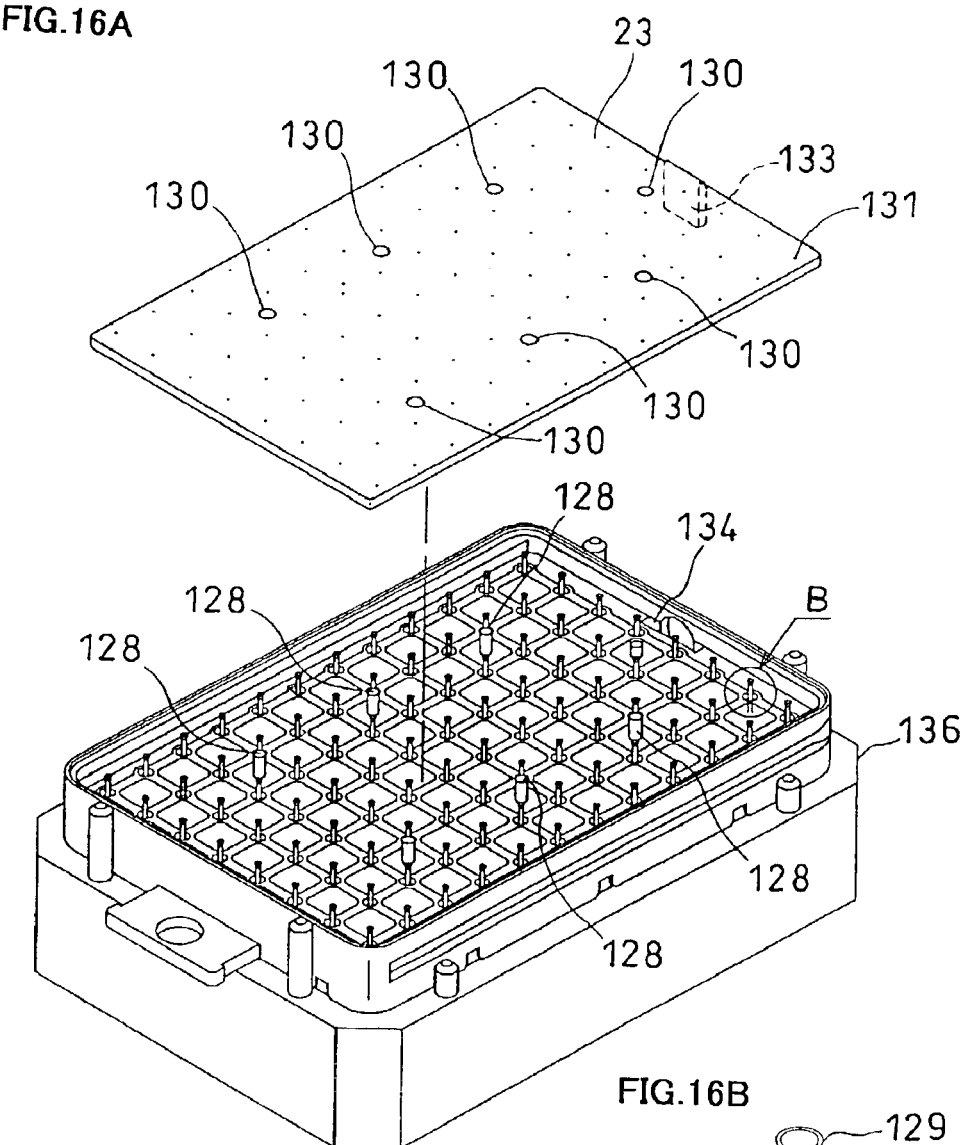
FIGS. 16A and 16B are views for illustrating a method for producing the load header according to Embodiment 2.

As shown in FIG. 16A, the connection plate is placed on the holder having the hollow electrodes bonded thereto while matching the protruding guide pins 128 of the holder with the corresponding holes 130 of the connection plate, thereby aligning the centers of the hollow electrodes with the centers of the respective insertion positions 131 of the connection plate. The tag 133 at the end of the rubber sheet is already bent to comply with the shape of the groove 134 of the holder and is inserted into the groove 134. The hollow electrodes are inserted in holes of a guide and the tips of the hollow electrodes are received and secured by a platform 136. The gap between the hollow electrodes and the holes are filled in with a resin to bond the hollow electrodes to the holder. As a result, the tips of the ninety-six hollow electrodes can be aligned with high precision.

Figure 16B:
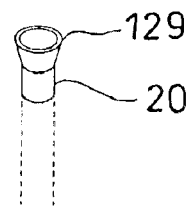

As shown in FIG. 16B, the tip of each hollow electrode has a flared shape with its diameter becoming narrower to the bottom. Large opening at the tip allows easy insertion of the capillaries into the hollow electrodes. Especially, the ninetysix capillaries can be inserted into the respective hollow electrodes easily after inserting the hollow electrodes into the connection plate and securing the lid thereon by ultrasonic bonding. This can be done since the distance between the capillary holes in the lid and the hollow electrodes is short and the openings at the tip of the hollow electrodes are larger than those of the capillary holes.

Figure 17A:
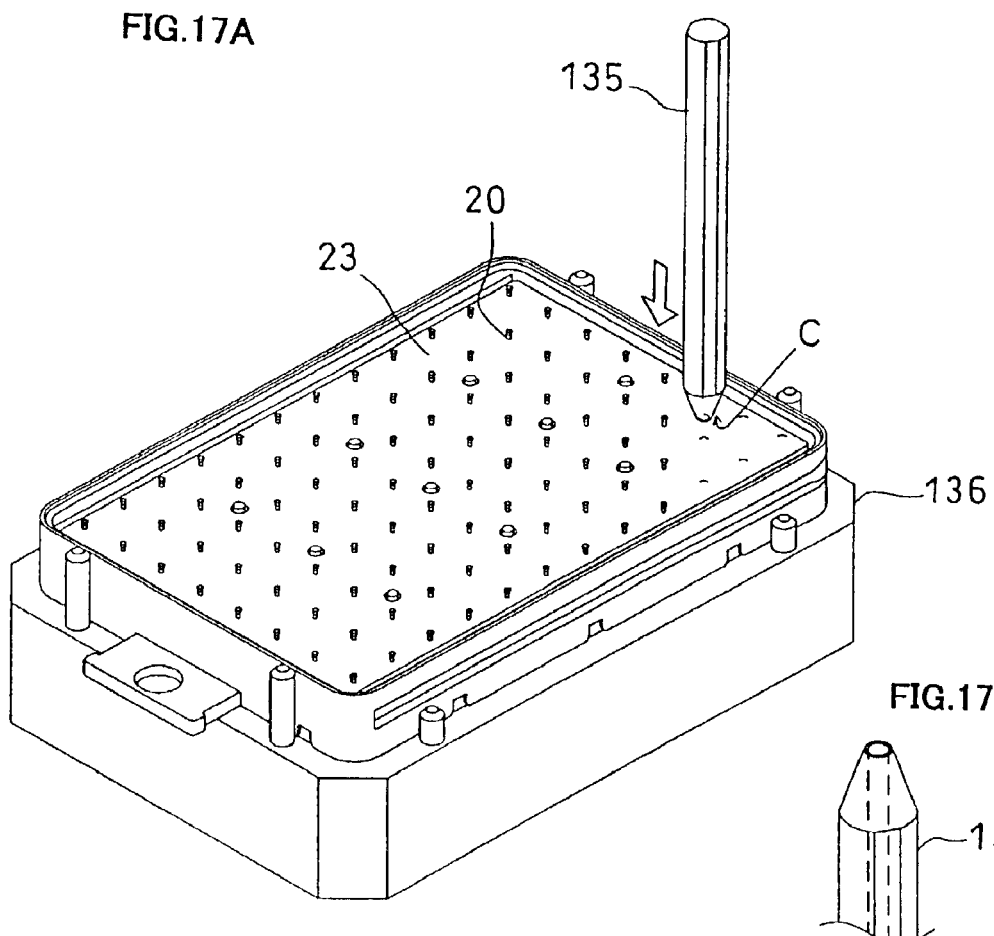
FIGS. 17A and 17B are views for illustrating the method for producing the load header according to Embodiment 2.

As shown in FIG. 17A, a hollow electrode insertion frame 135 having a hollow therethrough is placed one by one on the ninety-six insertion positions of the connection plate. Since the connection plate is pierced with a needle of about φ0.5 mm before insertion, the hollow electrodes can be inserted at the predetermined positions smoothly. Preferably, the insertion holes prior to insertion of the hollow electrodes 20 are closed due to the elasticity of the connection plate so that contact pressure on the hollow electrodes 20 can be enhanced. The hollow electrodes are inserted into the connection plate in direction indicated by the arrow (in the longitudinal direction of the hollow electrodes) while spreading out the parts of the connection plate surrounding the insertion positions, thereby breaking through the connection plate. As a result, a close contact between each hollow electrode and the connection plate can be obtained.

Figure 17B:
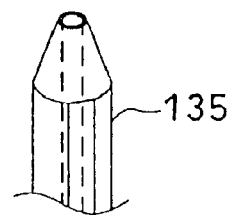

FIG. 17B is a view showing the shape of the inserted portion of the hollow electrode insertion frame 135. The inserted portion has a donut shape preferably with its inner diameter being slightly larger than the outer diameter of the hollow electrodes. If the inner diameter is smaller, the insertion becomes more difficult deteriorating operation efficiency. If the inner diameter is too large, it may rip off the part of the connection plate where it should be surrounding the hollow electrodes.

Figure 18:
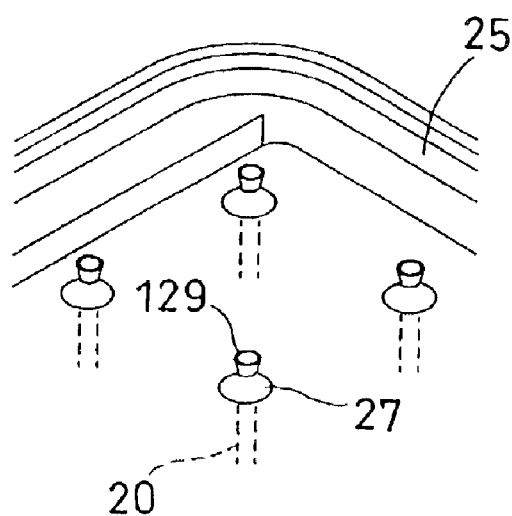
FIG. 18 is a view showing how to secure the hollow electrodes with the connection plate using an adhesive.

As shown in FIG. 18, an adhesive 27 is applied on the top of the connection plate and the hollow electrodes and cured. The adhesive is most preferably an inexpensive epoxy adhesive which has strength and good water resistance property. Accordingly, the contact member can be shielded from oxidizing atmosphere or moisture. Therefore, passive coating can be prevented from being generated or increasing, thereby suppressing deterioration of contact resistance. In addition, contact pressure between the hollow electrodes and the connection plate can be increased. This can prevent deterioration of the performance of the capillary arrays that are transported or stored under severe environment, for example, where the capillary arrays are transported by air in a cargo compartment of a plane where it would be below freezing temperature.

A conductive adhesive containing conductive particles may be used as the adhesive 27 so that the contact resistance between the hollow electrodes and the connection plate can be further minimized. Preferably, the conductive particle is silver, nickel, carbon or the like.

According to the present embodiment, the contact resistance between the hollow electrodes and the connection plate can be minimized. Therefore, fluctuations in the electrophoresis voltage applied to the samples in the capillaries which is caused depending on the stability of the high-voltage power source can be minimized. Moreover, the contact state between each hollow electrode and the connection plate can be uniform. As a result, separation ability of the electrophoresis apparatus can be enhanced.

Furthermore, according to the present embodiment, the hollow electrodes and the connection plate can be connected electrically in a very easy manner.

[Embodiment 3]

Figure 19A:
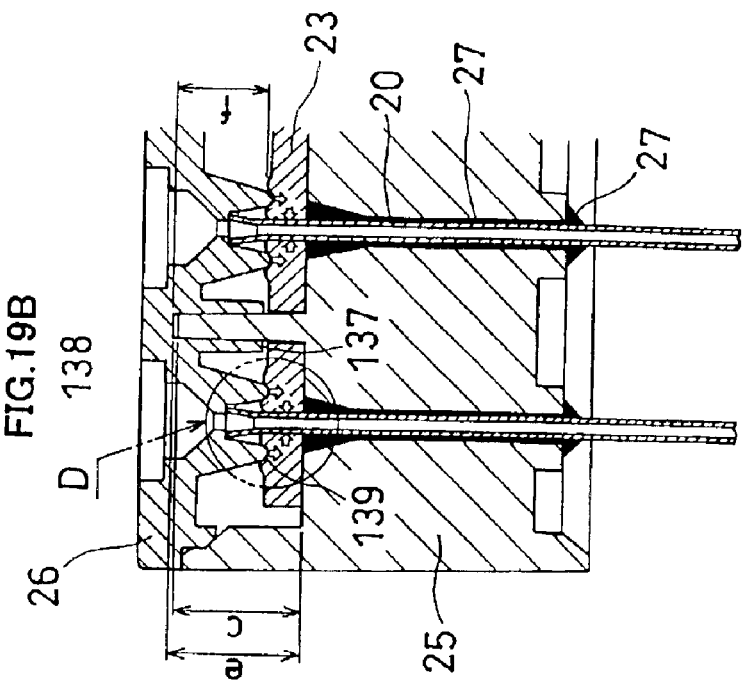
FIGS. 19A to 19D are views and a flowchart for illustrating a method for producing a load header according to Embodiment 3.
Figure 19B:
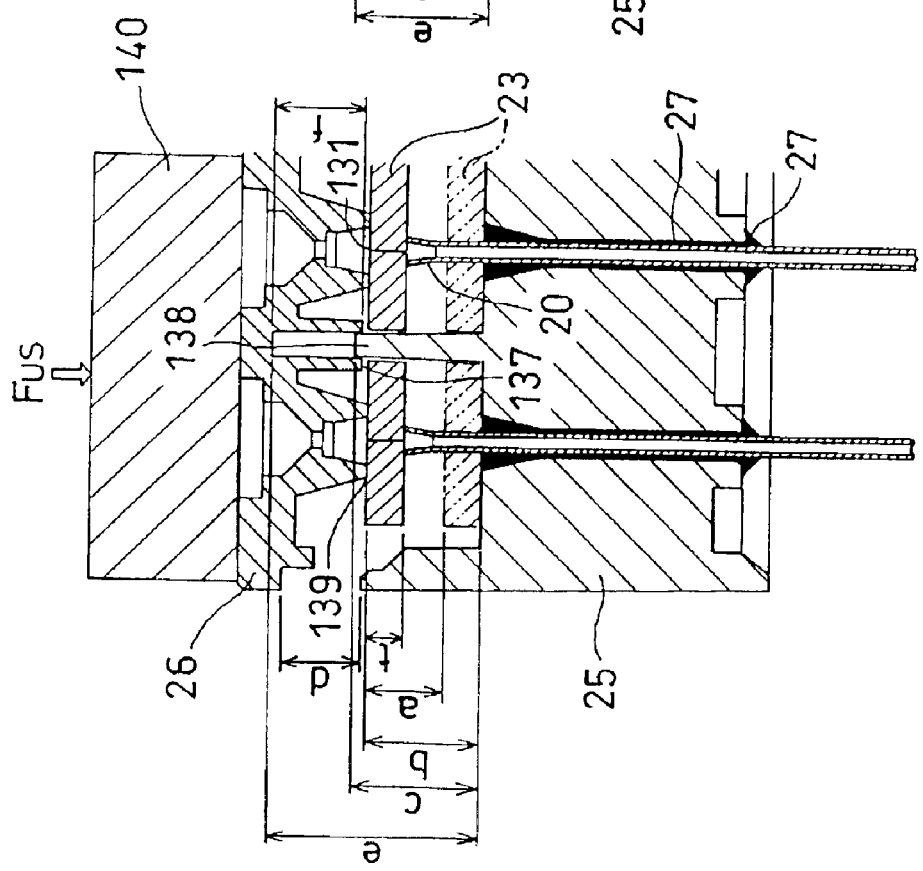
Figure 19C:
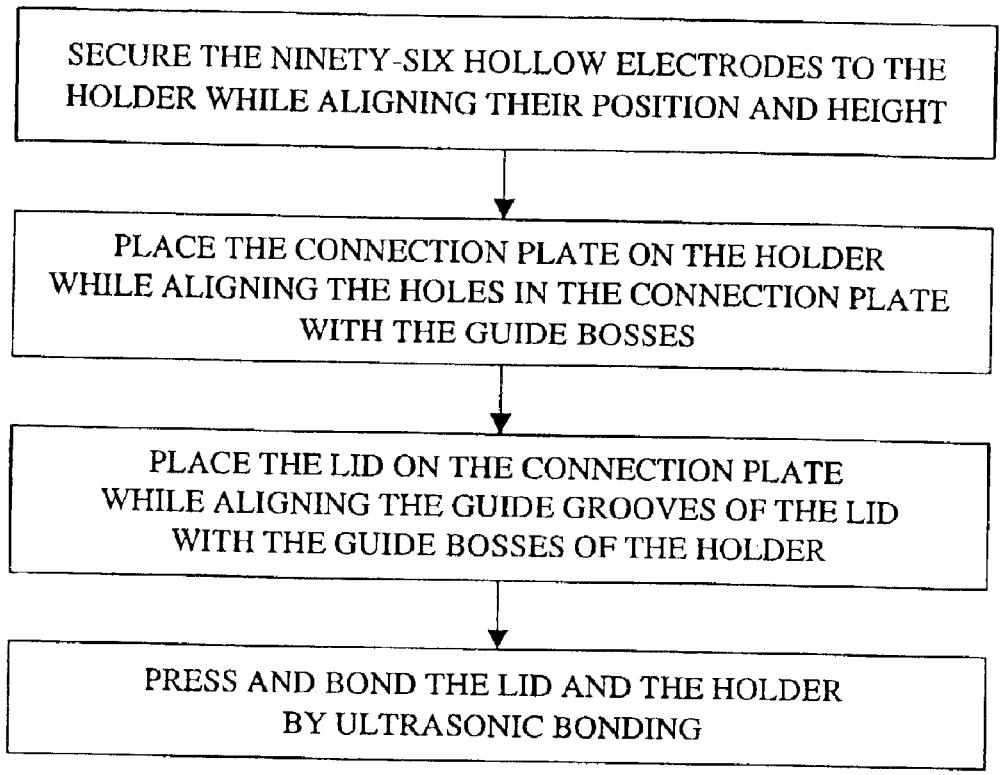
Figure 19D:
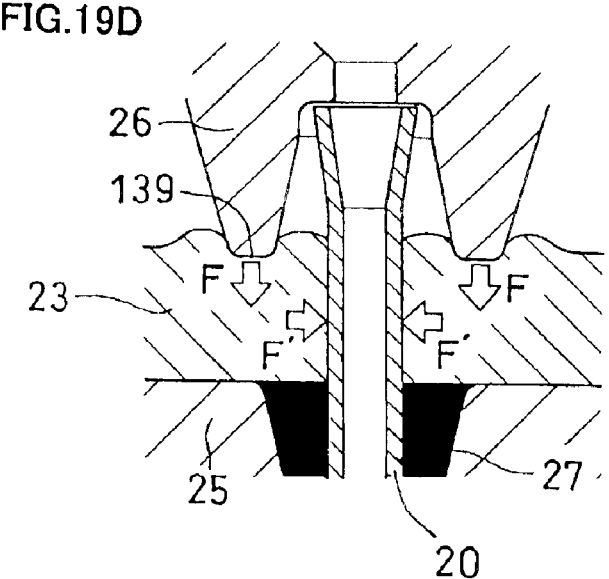

The present embodiment relates to a method for producing the load header in which the hollow electrodes are inserted into the insertion holes of the connection plate and the lid is secured to the holder by ultrasonic bonding at the same time. Hereinafter, the present embodiment will be described with reference to FIGS. 19A to 19D. FIG. 19A is a cross-sectional view showing a state prior to ultrasonic bonding; FIG. 19B is a cross-sectional view showing a state after the bonding; FIG. 19C is a flowchart of production; and FIG. 19D is a cross-sectional view showing a part near the hollow electrode after the bonding in detail.

In the same manner as Embodiment 2, ninety-six hollow electrodes 20 are secured to the holder 25. Then, as shown in FIG. 19A, the connection plate 23 and the lid 26 are placed in this order on the holder 25 where the ninety-six (12×8) hollow electrodes are accurately arranged and fixed with the adhesive. The insertion holes 130 of the connection plate 23 and the guide grooves 137 of the lid 26 are matched with multiple guide bosses 138 of the holder 25 so as to prevent positional shift among the holder 25, the connection plate 23 and the lid 26. At this point, the hollow electrodes are not yet inserted into the insertion holes of the connection plate.

Next, load is applied to the lid 26 with an ultrasonic horn 140. Circumferential ribs 139 provided for the lid 26 press the parts of the connection plate 23 surrounding the insertion holes 131 to press the hollow electrode 20 into the connection plate 23 until the connection plate 23 makes contact with the holder 25.

Finally, the circumferential ribs 139 continue to press the parts of the connection plate 23 surrounding the insertion holes 131 so that the holder 25 and the lid 26 make contact with each other. Immediately after that, the holder 25 and the lid 26 are bonded by ultrasonic bonding as shown in FIG. 19B. In this manner, the ninety-six hollow electrodes can be inserted through the connection plate by simply pressing the lid and the holder toward each other.

FIGS. 20A to 20C show the load header produced according to the above-described method. FIG. 20A is a partial front cross-sectional view showing the load header; FIG. 20B is a partial side cross-sectional view showing the load header; and FIG. 20C is a cross-sectional view showing part E in FIG. 20A in detail. According to the present embodiment, the ribs 139, the holder 25 and the connection plate 23 have predetermined dimensions so that the load header can be produced with the ribs 139 enhancing the pressure bonding between the hollow electrodes and the connection plate 23. With reference to FIG. 19D, the circumferential ribs 139 press the parts of the connection plate surrounding the hollow electrodes to apply force (F) to the connection plate 23 in the longitudinal direction of the hollow electrodes. Since the connection plate 23 is pushed to the opposite side from the ribs 139, volume elasticity (F') applied to the hollow electrodes 20 is increased. Accordingly, the pressure bonding between the hollow electrodes 20 and the connection plate 23 is also increased, thereby minimizing contact resistance. Since the load header is provided with a mechanism for pressing the parts of the connection plate surrounding the hollow electrodes, contact resistance at the contact interfaces between the hollow electrodes and the connection plate can be minimized.

When the ribs 139 are, for example, tubular with a concave cross-section and the hollow electrodes are present in the middle of the pressed parts of the connection plate (parts of the connection plate pressed by the ribs), the volume elasticity applied to the hollow electrodes will be increased in a generally uniform manner. Therefore, capillaries are easy to produce. Herein, a "part surrounding" refers to a region of the connection plate 23 where increase of the volume elasticity can be seen.

According to the above-described production method, once the shapes of the holder, the connection plate and the lid satisfy predetermined conditions, the lid can be inserted smoothly into the holder and the connection plate can be pressed. Hereinafter, the conditions (1) to (4) will be described based on the distances a to f shown in FIGS. 19A and 19B.

Herein, the distances a to f are defined as:
a distance from the top surface of the connection plate prior to ultrasonic bonding to the top surface of the connection plate after the ultrasonic bonding;
b distance from the top surface of the connection plate prior to the ultrasonic bonding to the bottom surface of the connection plate after the ultrasonic bonding;
c distance from the bottom surface of the connection plate after the ultrasonic bonding to the tip of the guide bosses;
d distance between counter faces of the holder and the lid prior to ultrasonic bonding;
e distance from the bottom surface of the connection plate after the ultrasonic bonding to the deepest surface of the guide groove of the lid is inserted;
f depth of the guide groove; and
t thickness of the connection plate.

[Condition (1); $b-a \leq t$]

This relationship represents dimensional condition for the pressed connection plate after the final assembly. If this relationship is satisfied, the ribs 139 after the ultrasonic bonding are either in contact with or pressing the connection plate 23. If the relationship is not satisfied, the ribs 139 after the ultrasonic bonding are not in contact with the connection plate 23.

[Condition (2); $a \leq d$]

This relationship represents dimensional condition for ultrasonic bonding between the holder and the lid. If this relationship is satisfied, the holder and the lid can be bonded to each other. If not, a gap is caused between the holder and the lid and thus they cannot be bonded to each other.

[Condition (3); $c > a+t$]

This relationship represents dimensional condition for aligning the guide bosses with respect to the guide grooves. If this relationship is satisfied, the tip of the guide boss should be protruding from the connection plate prior to ultrasonic bonding and thus the guide bosses can be fit in the guide groove, thereby preventing positional shift between the holder and the lid.

[Condition (4); $c+f > e$]

This relationship represents dimensional condition for determining the length of the guide bosses. If the relationship is not satisfied, the guide bosses will make contact with the guide grooves such that the holder and the lid cannot be bonded to each other.

According to the present embodiment, the mechanism for preventing positional shift is established by providing the protruding guide bosses 138 for the holder and the guide grooves 137 for the lid while the inner diameters of the holes in the connection plate are made generally equal to the outer dimensions of the guide bosses 138. However, the structure of the mechanism for preventing positional shift is not limited to this. Other examples will be described with reference to FIGS. 21A and 21B.

Figure 21A:
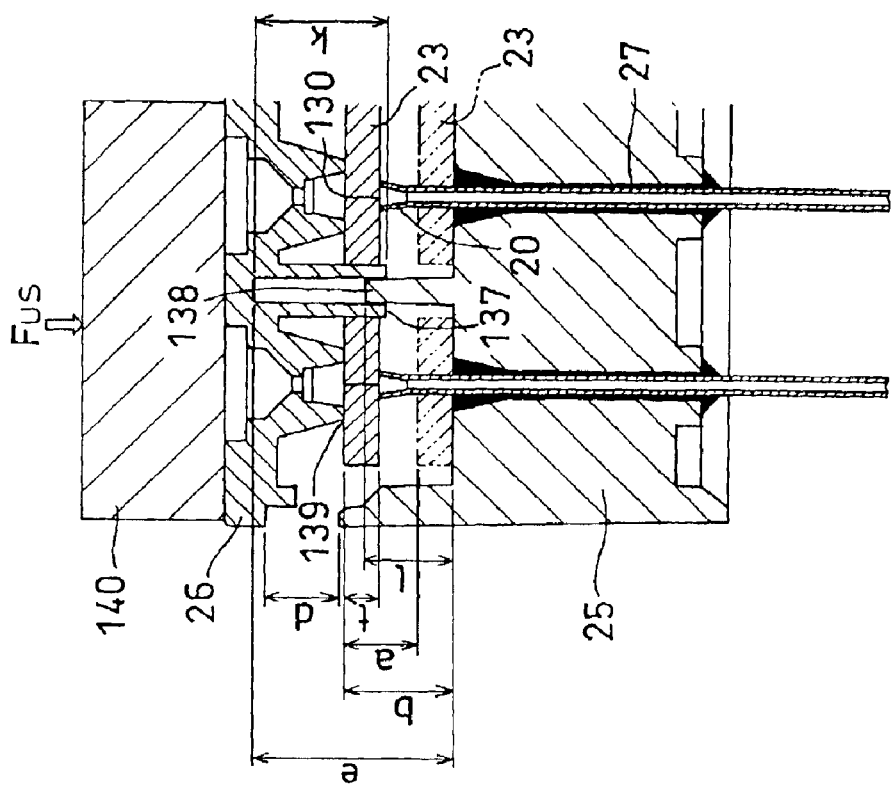
FIGS. 21A and 21B are cross-sectional views showing other examples of the method for producing the load header according to Embodiment 3.

FIG. 21A is a cross-sectional view showing a load header having a mechanism for preventing positional shift where the holder is provided with guide grooves having concaved centers and the lid is provided with guide bosses matching the guide grooves.

Figure 21B:
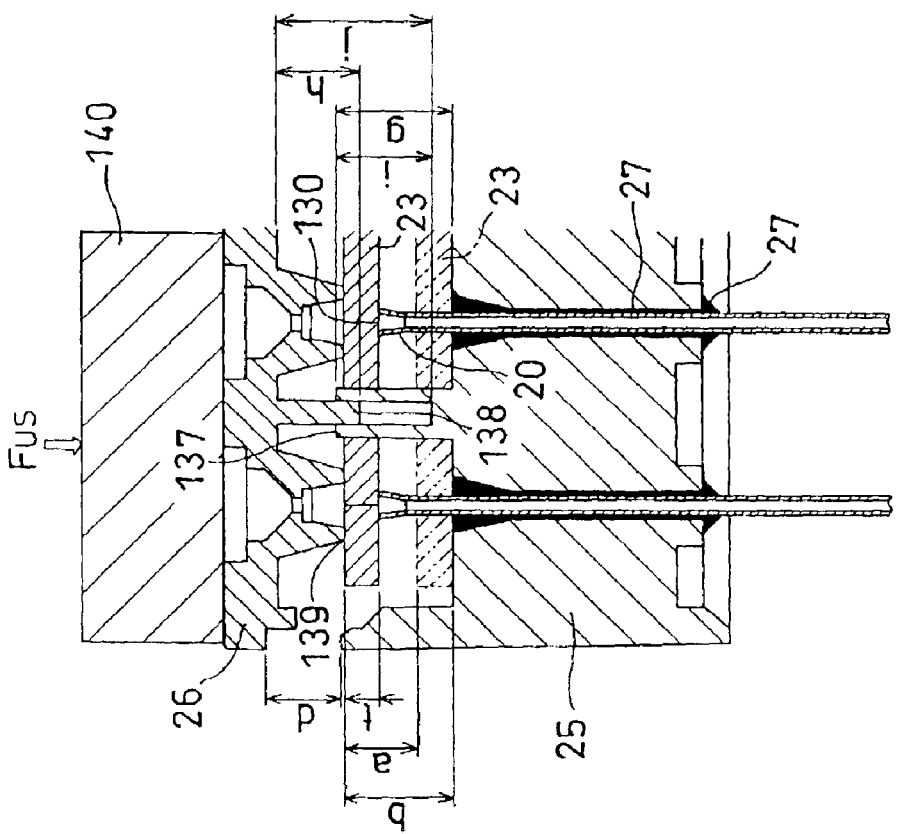

In this case, requirements will be as follows.
Condition (1); $b-a \leq t$
Condition (2); $a \leq d$
Condition (3); $g > a+t$
Condition (4); $h+i > j$ FIG. 21B is a cross-sectional view showing the load header where the lid is provided with guide grooves with concaved centers which match the holes in the connection plate. The diameter of the holes in the connection plate is smaller than that of the guide grooves for about 0.5 mm to prevent disconnection between them.

In this case, the conditions for smoothly inserting the lid into the holder will be as follows.

Condition (1); $b-a \leqq t$
Condition (2); $a \leqq d$
Condition (3); $k > a+t$
Condition (4); $l+k < e$ The g to l shown in FIGS. 21A and 21B are defined as:
g distance from the bottom surface of the connection plate after the ultrasonic bonding to the tip of the guide groove;
h length of the guide boss;
i depth of the guide groove;
j distance from the deepest surface of the guide groove to the root of the guide boss;
k depth of the guide groove; and
l distance from the bottom surface of the connection plate after the ultrasonic bonding to the tip of the guide boss; and
t thickness of the connection plate.

Furthermore, parts of the connection plate where they make contact with the hollow electrodes and the ribs may be indented (not shown). Thus, at least one of the holder, the connection plate and the lid serves to prevent relative movement in the longitudinal and transversal directions of the hollow electrodes with respect to the other members. Therefore, the hollow electrodes can be electrically connected to the connection plate while the holder and the lid are bonded together. In particular, since the ninety-six hollow electrodes and the connection plate can be connected in a generally uniform state, separation ability of the electrophoresis apparatus can be ensured.

According to the present embodiment, by pressing the holder and the lid toward each other, a load header of a capillary array can be produced in which the hollow electrodes and the connection plate make contact to each other via volume elasticity. Preferably, a capillary array is produced in which parts of the connection plate surrounding the hollow electrodes are pressed.

Thus, the present invention provides a highly reliable capillary array which has good separation ability and which can be produced easily, as well as an electrophoresis apparatus incorporating the capillary array.

What is claimed is:

1. A capillary array comprising:
    a plurality of capillaries having sample inlet ends from which a separation medium for separating a sample is filled in and from which the sample is introduced;
    a detection section, holding parts of the plurality of capillaries to be irradiated with laser light in parallel, wherein the parts of the capillaries allow transmission of the laser light for exciting the sample;
    a load header provided with hollow electrodes for holding the capillaries near the sample inlet ends of the capillaries, and a conductive connection member electrically connected to the hollow electrodes; and
    capillary heads for holding the other ends of the capillaries,
    wherein contact interfaces between the conductive connection member and the respective hollow electrodes are pressed by volume elasticity.

2. A capillary array according to claim 1, wherein the conductive connection member is made of a conductive rubber.

3. A capillary array according to claim 1, wherein the hollow electrodes are made of austenite stainless steel.

4. A capillary array according to claim 1, wherein the cross-section of the peripheral surface of the hollow electrodes is circular.

5. A capillary array according to claim 1, wherein the load header is provided with a pressing member.

6. A capillary array according to claim 5, wherein each of the hollow electrodes is present within each of the plurality of pressed parts that press the conductive connection member.

7. A capillary array according to claim 1, wherein one end of the hollow electrode has a flared shape.

8. A capillary array according to claim 1, wherein the conductive member is capable of contacting with a connector that is electrically connected with a power source for electrophoresis.

9. An electrophoresis apparatus, comprising;
    a capillary array, comprising;
        a plurality of capillaries, having a sample inlet end from which the sample is introduced;
        a detection section, holding parts of the plurality of capillaries;
        a load header, having hollow electrodes for holding the sample inlets; and a conductive connection member electrically connected with the hollow electrodes, and
        a capillary head, holding the other ends of the capillaries;
    a power source capable of electrophoresing samples in the plurality of capillaries;
    an excitation optical system capable of irradiating the detection section; and
    a detection lens systems capable of detecting light emitted from samples,
    wherein contact interfaces between the conductive connection member and the respective hollow electrodes are pressed by volume elasticity.

10. An electrophoresis apparatus according to claim 9, wherein the conductive connection member is made of a conductive rubber.

11. An electrophoresis apparatus according to claim 9, wherein the hollow electrodes are made of austenite stainless steel.

12. An electrophoresis apparatus according to claim 9, wherein the cross-section of the peripheral surface of the hollow electrodes is circular.

13. An electrophoresis apparatus according to claim 9, wherein the load header is provided with a pressing member.

14. An electrophoresis apparatus according to claim 13, wherein each of the hollow electrodes is present within each of the plurality of pressed parts that press the conductive connection member.

15. An electrophoresis apparatus according to claim 9, wherein one end of the hollow electrode has a flared shape.

16. An electrophoresis apparatus according to claim 9, wherein the conductive member is capable of contacting with a connector that is electrically connected with the power source.

17. A capillary array comprising;
    a plurality of capillaries, having a sample inlet end from which the sample introduced;
    a detection section, holding parts of the plurality of capillaries to be irradiated with light;
    a load header, having hollow electrodes for holding the sample inlets, and a conductive connection member electrically connected with the hollow electrodes; and a capillary head, holding the other ends of the capillaries,
wherein the conductive connection member is made of conductive rubber or conductive plastic.

18. A capillary array according to claim 17, wherein the hollow electrodes are made of austenite stainless steel.

19. A capillary array according to claim 17, wherein the conductive connection member is a conductive connection plate.

20. A capillary array according to claim 17, wherein a plurality of nail springs of the conductive connection member, which are symmetrically provided around each of the hollow electrodes, make contact with an outer surface of the hollow electrodes.

21. A capillary array according to claim 20, wherein a pressure at interfaces between the outer surface of the hollow electrodes and the nail springs of the conductive connection member is 5 to 10 MPa.

22. A capillary array according to claim 21, wherein an adhesive is applied and cured on the interface between the contact parts of the hollow electrodes and the nails of the conductive connection part.

23. A capillary array according to claim 17, wherein the hollow electrodes are inserted in the conductive connection member.

24. A capillary array according to claim 23, wherein contact interfaces between the conductive connection member and the respective hollow electrodes are pressed by volume elasticity.

25. An electrophoresis apparatus, comprising;
   a capillary array, comprising;
      a plurality of capillaries, having a sample inlet end from which the sample is introduced;
      a detection section, holding parts of the plurality of capillaries to be irradiated with light;
      a load header, having hollow electrodes for holding the sample inlets, and a conductive connection member electrically connected with the hollow electrodes; arid
      a capillary head, holding the other ends of the capillaries;
   a power source capable of electrophoresing samples in the plurality of capillaries;
   an excitation optical system capable of irradiating the detection section; and
   a detection lens system capable of detecting light emitted from samples,
   wherein the conductive connection member is made of conductive rubber or conductive plastic.

26. An electrophoresis apparatus according to claim 25, wherein the hollow electrodes are made of austenite stainless steel.

27. An electrophoresis apparatus according to claim 25, wherein the conductive connection member is a conductive connection plate.

28. An electrophoresis apparatus according to claim 25, wherein a plurality of nail springs of the conductive connection member, which are symmetrically provided around each of the hollow electrodes, make contact with an outer surface of the hollow electrodes.

29. An electrophoresis apparatus according to claim 28, wherein a pressure at interfaces between the outer surface of the hollow electrodes and the nail springs of the conductive connection member is 5 to 10 MPa.

30. An electrophoresis apparatus according to claim 28, wherein an adhesive is applied and cured on the interface between the contact parts of the hollow electrodes and the nails of the conductive connection part.

31. An electrophoresis apparatus according to claim 30, wherein contact interfaces between the conductive connection member and the respective hollow electrodes are pressed by volume elasticity.

32. An electrophoresis apparatus according to claim 25, wherein the hollow electrodes are inserted in the conductive connection member.

\* \* \* \* \*